US00PP28466P3

(12) United States Plant Patent
Gerdts et al.

(10) Patent No.: US PP28,466 P3
(45) Date of Patent: Oct. 3, 2017

(54) ALMOND TREE NAMED 'BURALMONDTWO'

(50) Latin Name: *Prunus dulcis*
Varietal Denomination: Buralmondtwo

(71) Applicants: Timothy J. Gerdts, Kingsburg, CA (US); John K. Slaughter, Fresno, CA (US)

(72) Inventors: Timothy J. Gerdts, Kingsburg, CA (US); John K. Slaughter, Fresno, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 49 days.

(21) Appl. No.: 14/756,674

(22) Filed: Sep. 29, 2015

(65) Prior Publication Data
US 2017/0094853 P1 Mar. 30, 2017

(51) Int. Cl.
*A01H 5/08* (2006.01)

(52) U.S. Cl.
USPC ..... Plt./155

(58) Field of Classification Search
USPC ..... Plt./155
See application file for complete search history.

*Primary Examiner* — Keith Robinson
(74) *Attorney, Agent, or Firm* — Randall Danskin P.S.

(57) ABSTRACT

A new and distinct variety of almond tree is described, and which is denominated varietally as 'Buralmondtwo', and which further expresses self-fertility, and further produces well-sealed nuts which are mature for harvesting and shipment approximately July 27th to August 8th under the ecological conditions prevailing in the San Joaquin Valley of Central California.

3 Drawing Sheets

Latin name: '*Prunus dulcis*'.
Varietal denomination: 'Buralmondtwo'.

BACKGROUND OF THE NEW VARIETY

The present invention relates to a new, novel and distinct variety of Almond tree, and which has been denominated varietally as 'Buralmondtwo'.

ORIGIN AND ASEXUAL REPRODUCTION OF THE NEW VARIETY

The present variety of almond tree resulted from an on-going program of fruit and nut tree breeding. The purpose of this program is to improve the commercial quality of deciduous fruit and nut varieties, and rootstocks, by creating and releasing promising scion and rootstock selections of *Prunus, Malus, Punica* and *Juglans* species. To this end we make both controlled and hybrid cross pollinations each year in order to produce seedling populations from which improved progenies are evaluated and selected. After close field observation, and following this procedure, one seedling, 'Buralmondtwo', was selected from one of the several populations which were planted in our experimental orchards near Fowler, Calif. for further experimentation.

The aforementioned seedlings, grown on their own roots, were derived from a cross, made in February 2001, using the 'Tuono' (nonpatented), almond tree, and which was used as the seed parent; and a self-fertile almond tree, (unpatented), and which was named 'B1.005'. 'Tuono' is an unpatented almond tree which originated in Italy. The variety 'B1.005' was used as the pollen parent. After a period of stratification, the seeds were germinated, grown in our greenhouses, and then field planted by population for tree establishment, and ultimately to express the potential tree characteristics, and nut phenology for further evaluation. One self-fertile seedling, which is the present variety, exhibited especially desirable characteristics, and was subsequently designated as 'P10.022'. This seedling was marked for subsequent observation. After the 2004 fruiting season, the newly discovered variety of almond tree was selected for advanced evaluation, and asexual repropagation.

ASEXUAL REPRODUCTION

Asexual reproduction of this new and distinct variety of Almond tree was accomplished by budding the new almond tree onto 'Nemaguard' Rootstock (un-patented). This was performed by us in our experimental orchard which is located near Fowler, Calif. Subsequent evaluations of these first asexually reproduced plants have shown those asexual reproductions run true to the original tree. All characteristics of the original tree, and its crop, were established, and appear to be transmitted through these succeeding asexual propagations.

SUMMARY OF THE NEW VARIETY

'Buralmondtwo' is a new and distinct variety of almond tree, which is considered to be of medium-large size, and which further has a moderately vigorous growth characteristic. This new tree is also a regular and productive bearer of relatively large, very light colored nuts which have a very good flavor, and the tree is further considered productive. This new almond tree has a medium-low chilling requirement of approximately 300 hours, and further produces relatively uniformly sized nuts throughout the tree's canopy. In addition to the foregoing, the nuts of the new almond tree also appear to have good processing and shipping qualities. The 'Buralmondtwo' almond tree bears nuts which are typically ripe for commercial harvesting and hulling on approximately July 27 to August 8 under the ecological conditions prevailing in the San Joaquin Valley of central California. In relative comparison to the 'Nonpareil' almond tree, unpatented, and which is the closest known variety, the new variety of almond tree is self-fertile (the 'Nonpareil' almond tree is not self-fertile). Additionally, the Almond tree 'Buralmondtwo' produces a well-sealed shell which provides more protection from insect damage than that which is produced by the 'Nonpareil' Almond tree (unpatented), as well as other commercially grown almond varieties. In comparison to the seed parent, 'Tuono' (unpatented), the current variety blooms five days or more before the variety 'Tuono' at the same geographical location. Further, and in comparison to the pollen parent 'B1.005', (unpatented), the current variety harvests ten or more days earlier at the same geographical location.

BRIEF DESCRIPTION OF THE DRAWINGS

The accompanying drawings, which are provided, are color photographs of the new variety of Almond tree.

FIG. 1 depicts four (4) whole shelled almonds, one of which is resting in a half shell, and two (2) unshelled almonds, and two (2) unhulled/unshelled samples. Of the shelled and displayed samples four (4) kernels are exposed in a lateral view, and which demonstrates the kernel veining, the relative shape and the pellicle color. Further one (1) kernel is set on its ventral edge and provides a view of the kernel from the dorsal perspective. Additionally one (1) kernel is bisected, and placed on its apex, and further provides a view of the basal region. Moreover, one almond (including the shell) has been bisected in a horizontal plane and displays a cross-section of the shell, the inner seal, the kernel, its internal color, and the relative space between the kernel and the shell.

Figure 1:
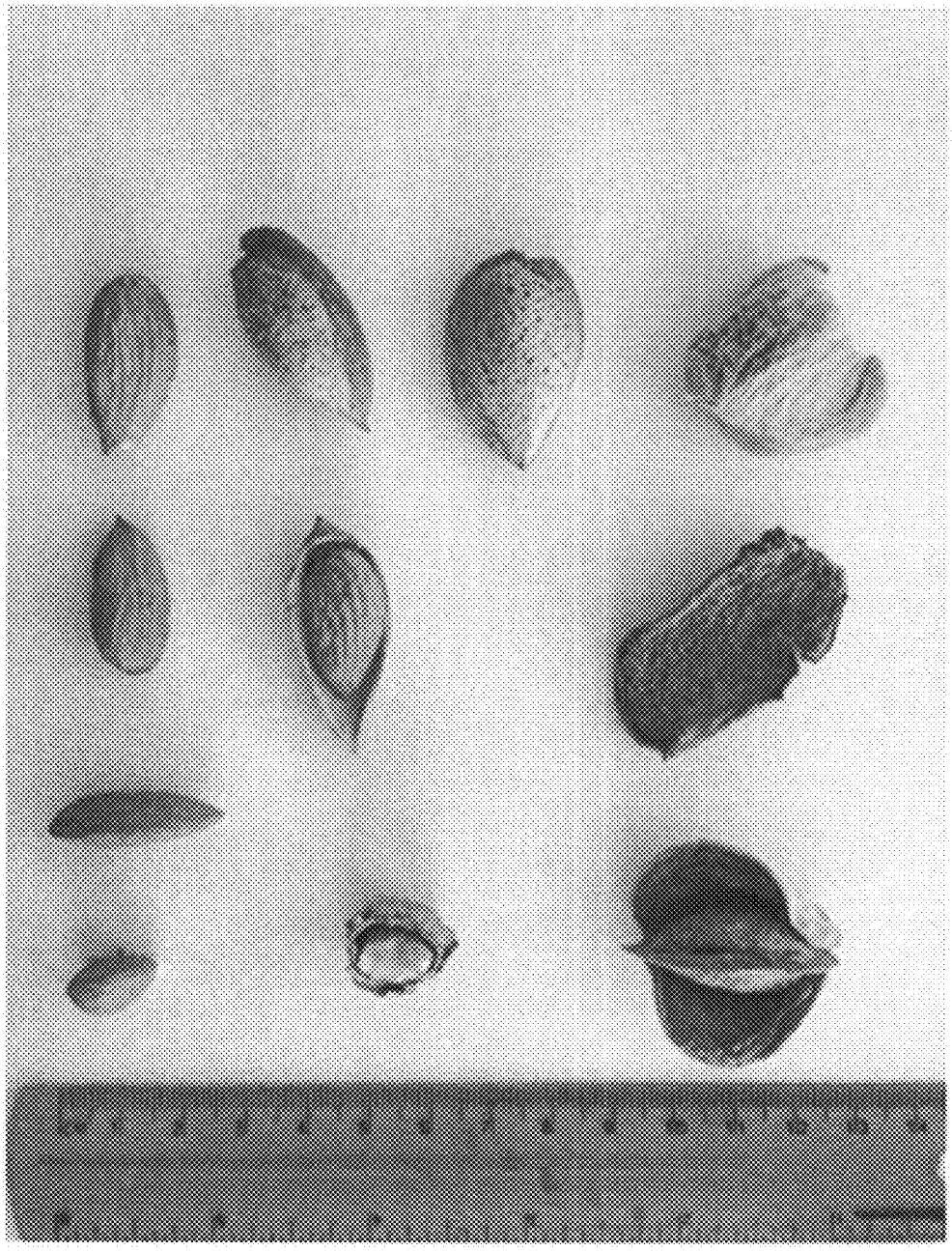
FIG. 1 depicts kernels, shells and hulls of the new almond tree variety. The nuts, shells and hulls are shown sufficently matured for harvest.
Figure 2:
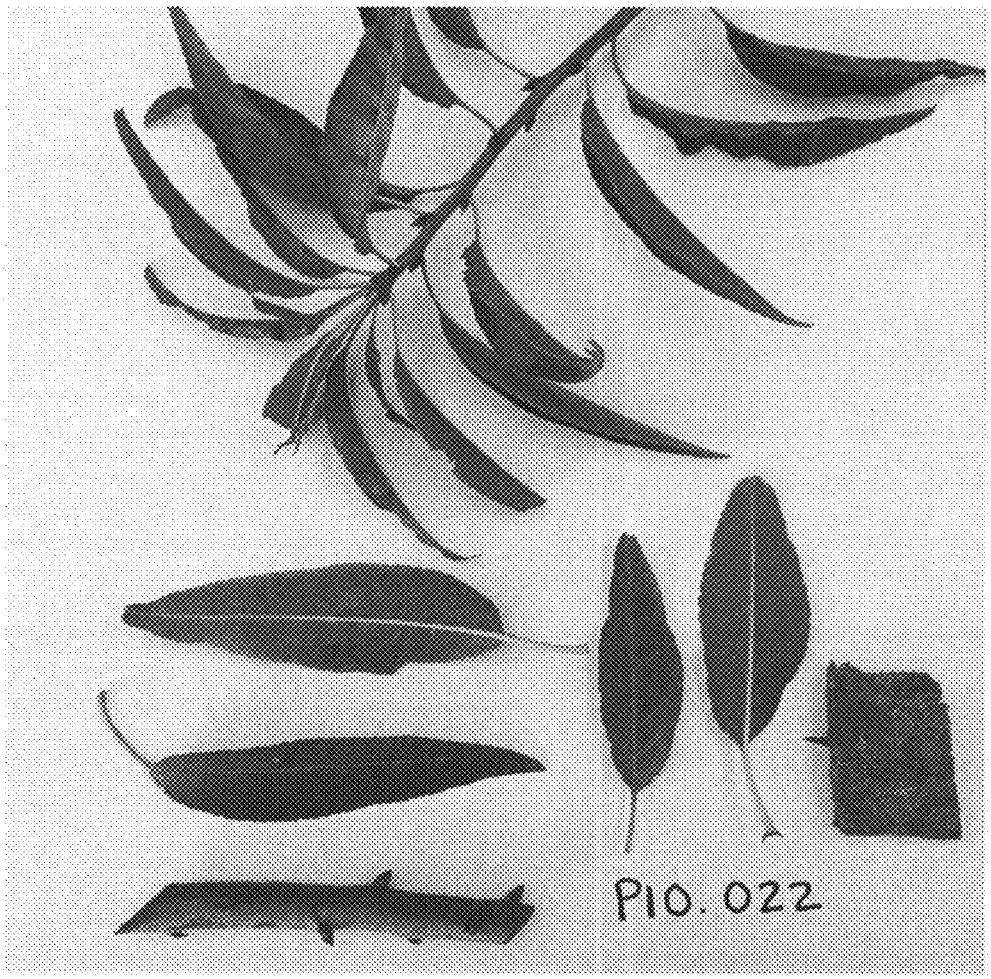
FIG. 2 depicts a twig bearing typical leaves, and several other leaves showing the dorsal and ventral coloration thereof.
Figure 3:
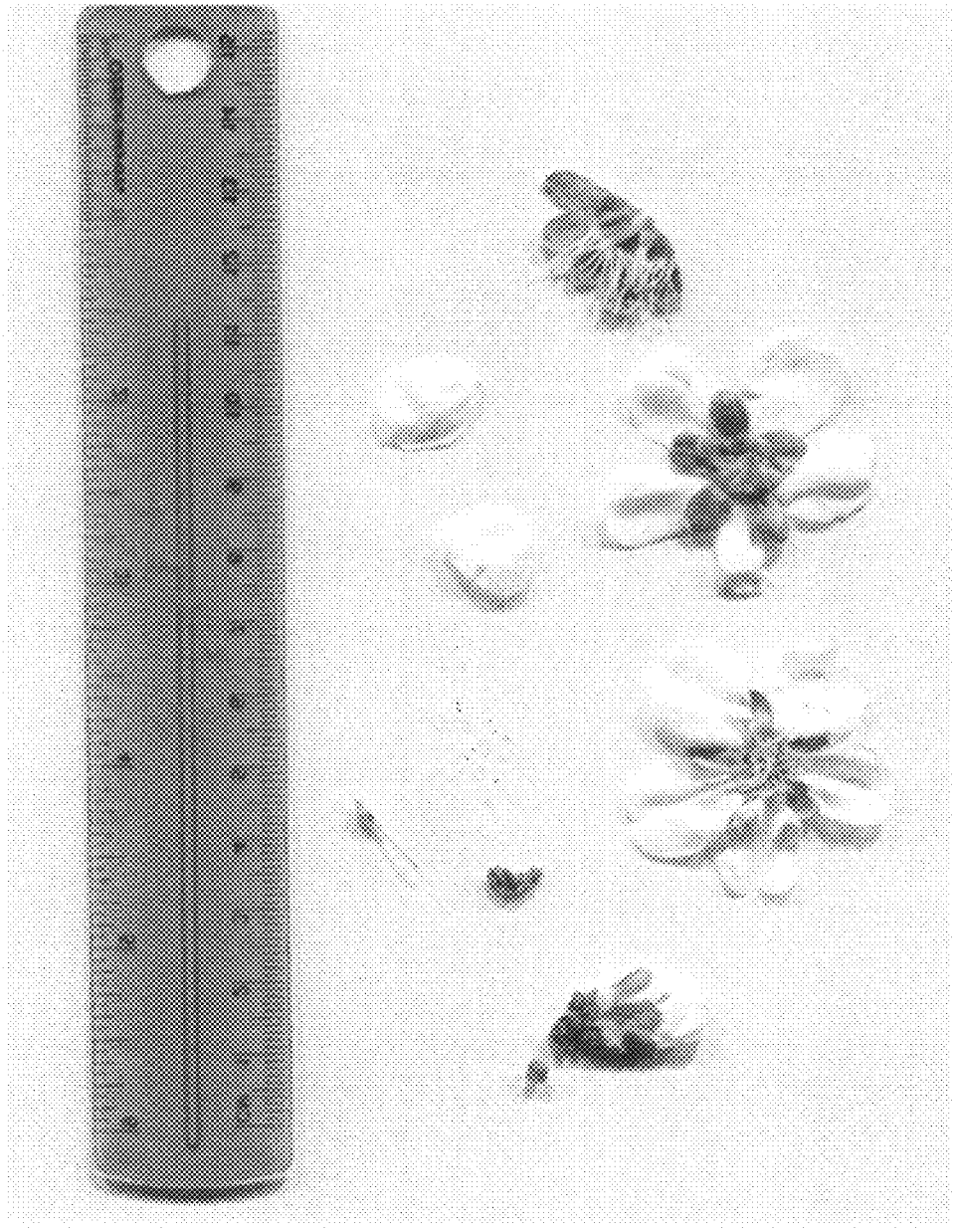
FIG. 3 depicts a typical flower produced by the new variety of Almond tree.

The colors in these photographs are as nearly true as is reasonably possible in a color representation of this type. Due to chemical development, processing and printing, the leaves and nuts depicted in these photographs may, or may not, be accurate when compared to the actual specimen. For this reason, future color references should be made to the color plates (Royal Horticultural Society, Fourth Edition, 2001), and descriptions provided, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will, in the future, display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of Almond tree, the following has been observed during the 12th fruiting season, and under the ecological conditions prevailing at the orchards of the assignee, and which are located near the town of Fowler, county of Fresno, state of Calif. All major color code designations are by reference to The R.H.S. Colour Chart (Fourth Edition, 2001), and which is provided by The Royal Horticultural Society of Great Britain. Common color names are also occasionally used.

Tree:

*Size*.—Generally considered medium-large in its growth pattern as compared to other common commercial almond cultivars. The Tree Height is approximately 6.0-7.0 meters; and the Tree Width is approximately 5.0-6.0 meters. The resulting tree size can vary based upon the prevailing cultural practices, and the influence of employed rootstocks, and the surrounding soil fertility.

*Vigor*.—Considered vigorous. The tree height in the first growing season was approximately 2.0 meters.

*Tree form*.—Spreading and more open than the 'Nonpareil' Almond tree (non-patented).

*Branching habit*.—The present tree has a prolific branching habit. Primary limb angles are approximately 45 to 55 degrees when measured from the horizontal plane. The displayed branching characteristic is similar to the 'Tuono' Almond tree, (unpatented).

*Productivity*.—Productive. The present tree typically produces more kilograms of nuts per tree than the 'Nonpareil' Almond tree, (non-patented), when these same trees are grown under similar environmental conditions. Tree productivity can vary with the prevailing cultural practices, and soil fertility. Consequently productivity is not a reliable botanical indicator for the present variety.

*Regularity of bearing*.—Regular. The fruit set has been adequate during the previous years of observation.

*Fertility*.—Self-fertile. Self-fertility has been confirmed in each of the previous 12 fruiting years which have been observed.

*Density*.—The present variety is not considered to have a dense canopy. New, current season growth tends to produce laterally extending buds, and which increase the fruit wood potential especially along the limbs and branches. The limb and canopy density can be significantly influenced by pruning (including using both heading and thinning cuts) and/or by employing mechanical topping.

*Hardiness*.—The present tree was grown and evaluated in USDA Hardiness Zone 9. The calculated winter chilling requirements of the new tree is approximately 300 hours at a temperature of at or below 7.0 degrees C. The present variety appears to be hardy under typical central San Joaquin Valley climatic conditions.

Trunk:

*Diameter*.—Approximately 25.5 cm in diameter when measured at a distance of approximately 15.24 cm. above the soil level. This measurement was taken at the end of the tenth growing season.

*Bark texture*.—Considered moderately rough. Since bark development, and bark coloration change with advancing tree age, this characteristic varies with the tree vigor, age and ambient environmental conditions. Therefore, this tree characteristic is not a dependable descriptor of the new variety.

*Lenticels*.—Numerous flat, oval lenticels are present. The observed lenticels range in size from approximately 4.0 millimeters to about 8.0 mm. in width; and between about 1.0 and about 2.0 millimeters in height.

*Lenticel color*.—Considered an orange brown, (RHS Greyed-Orange Group 170 A).

*Bark coloration*.—Variable, but it is generally considered to be a greyed brown, (RHS Greyed-Brown Group 200 D).

Branches:

*Size*.—Considered medium for the variety.

*Branch diameter*.—Average as compared to other Almond varieties. The branches typically have a diameter of about 14.0 centimeters when measured during the tenth year after grafting.

*Surface texture*.—Current season's, and new growth, are both considered smooth.

*Internode length*.—Approximately 2.0 cm.

*Color of mature branches*.—Grey-brown, (RHS Brown Group 199 C).

*Current seasons shoots*.—Color — Medium-light green, (RHS Yellow-Green Group 143 B). The color of new shoot tips will continue to darken to a greyed-red as the growing season progresses, (RHS Greyed-Red Group 178 B). Feathering of the shoots is strong.

Leaves:

*Size*.—Considered medium-large for the species. Leaf measurements have been secured from vigorous, upright, current-season growth, and which is taken at approximately mid-shoot. It should be understood that the leaf size is often influenced by prevailing growing conditions, quality of sunlight, and the location of the leaf within the tree canopy. For this reason, leaf sizes can vary significantly based upon the ambient, and other cultural factors, listed above, and are therefore not typically considered a dependable botanical descriptor.

*Leaf length*.—Approximately 100.0 to about 115.0 millimeters.

*Leaf width*.—Approximately 21.0 to about 25.0 millimeters.

*Leaf base-shape*.—The leaves generally exhibit an oblique marginal symmetry relative to the leaf longitudinal axis.

*Leaf form*.—Lanceolate.

*Leaf tip form*.—Acuminate.

*Leaf color*.—Upper Leaf Surface — Dark green, (approximately RHS Green Group 135 A).

*Leaf texture*.—Upper and lower leaf surfaces are glabrous.

*Leaf color*.—Lower Leaf Surface — A light to medium green color, (approximately RHS Green Group 135 A).

*Leaf venation*.—Pinnately veined.

*Mid-vein*.—Color — Considered a light, whiteish-green, (approximately RHS Green-White Group 157 B) during the early to mid-season period of growth.

*Leaf margins*.—Generally flat, and not considered undulating, when the tree is observed, and has previously received adequate hydration.

*Leaf form*.—Considered crenate.

*Leaf uniformity*.—Considered generally uniform.

*Leaf thickness*.—Considered medium for the species.

Leaf petioles:

*Form*.—Considered canaliculated, and having a more pronounced trough when viewed from the dorsal aspect. The petiole margin is considered rounded when viewed from the ventral aspect.

*Size*.—Considered large for the species.

*Length*.—About 14.0 to about 21.0 mm.

*Diameter*.—About 1.5 to about 2.5 mm.

*Color*.—Light yellow-green, (approximately RHS Green Group 142 D).

Leaf glands:

*Size*.—Considered small for the species; approximately 1.0 mm. in length; and about 1.0 mm. in height.

*Number*.—Generally one gland per marginal side is found. Observations of more than two glands per marginal side are more uncommon.

*Shape*.—Glands located at the base of the leaf are predominantly globose in shape.

*Color*.—Considered a medium-brown, approximately (RHS Grey-Orange Group 165 B).

Leaf stipules:

*Size*.—Leaf stipules are "medium" in size. Stipule length is approximately 6.0-7.0 mm; and stipule width is approximately 1.0-1.5 mm.

*Number*.—Typically two per leaf bud, and up to six (6), or more, per shoot tip.

*Form*.—Lanceolate in form, and having a serrated marginal edge.

*Color*.—Green, (approximately RHS Green Group 139 B) when young, but graduating to a brown color, (approximately RHS Greyed-Orange Group 165 A) with advancing senescence. The leaf stipules are generally considered to be early deciduous.

Flower buds:

*Hardiness*.—No winter injury (bud death) has been noted during the last several years of observation in the central San Joaquin Valley. The new variety of Almond tree has not been intentionally subjected to drought, cold or heat stress, and therefore this information is not available.

*Flower bud*.—Size — Variable, and dependent upon the state of maturity. The flower buds, as described, were observed approximately seven (7) days prior to bloom.

*Flower bud*.—Length — Approximately 14.0 millimeters.

*Flower bud*.—Diameter — Approximately 8.5 millimeters.

*Flower bud surface texture*.—Pubescent.

*Flower bud orientation*.—Considered appressed, but this appears less so as the blossoms near the season for opening.

*Bud scale color*.—Considered a Brownish-purple, (Approximately RHS Greyed-Orange Group 166 A).

*Flower bud shape*.—Ovatus. (Description from *Botanical Latin* by William T. Stearn, 4th Edition, page 310, diagram "D").

*Distribution of flower buds*.—Flower buds occur equally on spurs and on one year old shoots.

Flowers:

*Date of first bloom*.—Observed on Feb. 12, 2015.

*Blooming time*.—Considered earlier than average in relative comparison to other commercial almond cultivars grown in the central San Joaquin Valley. The date of full bloom was observed on Feb. 19, 2015. The bloom date can vary, from season-to-season, subject to the accumulated chilling hour requirements, and also the number heat units received during the prebloom interval. The date of full bloom varies slightly with climatic conditions, and the prevailing cultural practices. It should be noted that in regions of lower chilling hour accumulation, the bloom of 'Buralmondtwo' will advance as compared to the bloom period of the 'Nonpareil' Almond tree, (nonpatented), and which is growing in the same geographical area. Conversely, and when the new tree is planted in areas with a higher chilling hour accumulation, and cooler prebloom temperatures, the 'Buralmondtwo' Almond tree, and the 'Nonpareil' Almond, (nonpatented), display bloom dates which are more closely similar.

*Duration of bloom*.—Approximately 11 days or more. This particular characteristic varies slightly with the prevailing climatic conditions.

*Flower class*.—Considered a perfect flower, complete and perigynous.

*Flower type*.—The variety is considered to have a showy-type flower.

*Flower size*.—Considered medium-large for the species. The flower diameter at full bloom is approximately 30.0 to 38.0 millimeters. The flower height at full bloom, is approximately 19.0 to 22.0 mm.

*Bloom quantity*.—Considered abundant.

*Flower bud frequency*.—Normally one to multiple flower buds appears per node/spur. Occasionally only one flower bud per node is observed.

*Petal size*.—Generally considered medium sized for the species.

*Petal length*.—Approximately 14.0 to 16.0 millimeters.

*Petal width*.—Approximately 16.0 to 18.0 millimeters.

*Petal form*.—Considered broadly ovate.

*Petal count*.—Nearly always 5.

*Petal texture*.—Both the upper and lower surfaces of the petal texture are considered weakly glabrous and reveal a moderately shiny, satiny surface.

*Petal color*.—Considered a dull white at the popcorn stage, (RHS White Group N155 A).

*Fragrance*.—Slight.

Petal claw:

*Form*.—The claw is considered truncate, and is generally medium-small when compared to other varieties.

*Length*.—Approximately 9.0-11.0 millimeters.

*Width*.—Approximately 8.0 to 10.0 millimeters.

*Petal margins*.—Shape — Generally considered variable, from nearly smooth to moderately undulate.

*Petal apex*.—Surface Texture — Generally, the petal margin is grooved at the tip.

*Width*.—About 3.0-5.0 millimeters.

*Depth*.—About 1.0-3.0 millimeters.

Flower pedicel:

*Length*.—Considered medium-long with an approximate length of about 2.5 to about 4.0 millimeters.

*Diameter*.—Approximately 2.0 millimeters.

*Color*.—A medium-brown, approximately (RHS Grey-Brown Group 199 A).

*Surface texture*.—Glabrous.

Floral nectaries:

*Color*.—Considered a deep orange color, (approximately RHS Greyed-Orange Group 173 C).

Calyx:

*Surface texture*.—Generally glabrous.

*Color*.—A dull green, (approximately RHS Green Group 138 B).

Sepals:

*Surface texture*.—The surface has a short, fine pubescent texture.

*Number*.—Five (5) sepals are present.

*Size*.—Average, and ovate in form.

*Sepal length*.—Approximately 6.0 to 7.0 millimeters.

*Sepal width*.—Approximately 5.0 to 6.0 millimeters.

*Sepal shape*.—Generally obovate.

*Sepal margin*.—Considered smooth and entire.

*Sepal color*.—A dull, magenta, (approximately RHS Greyed-Red Group 181 B).

Anthers:

*Size*.—Considered average. Length of anther is approximately 1.5-2.0 mm and the width of the anther is approximately 1.0-1.5 mm.

*Color*.—Red to Greenish Yellow in color when viewed dorsally, and prior to dehiscence, (approximately RHS Yellow-Group 144 C).

*Pollen production*.—Pollen is abundant, and has a yellow color, (approximately RHS Yellow-Orange Group 12 C).

*Fertility*.—Self-fertile.

*Position of stigma*.—The stigma is generally 1.0-1.2 mm above the anthers.

Filaments:

*Size*.—Approximately 9.0 to 11.0 millimeters in length; and approximately 0.5-0.7 millimeters in width.

*Color*.—Considered white, (RHS White Group N155 B).

Pistil:

*Number*.—Usually one, and only rarely more than one, is observed.

*Size*.—Generally, medium in size.

*Length*.—Approximately 11.0 to about 12.5 millimeters in length including the ovary.

*Color*.—Considered a very pale green, (approximately RHS Yellow-Green Group 150 A).

*Surface texture*.—The variety has a long pubescent pistil.

Nut crop:

*Productivity*.—Very productive. The new Almond tree variety is very precocious. The production of the instant BURALMONDTWO Almond, compared to Nonpareil (same age tree on the same rootstock) during the first six (6) years after planting. BURALMONDTWO showed approximately 20% increase yield in comparison to Nonpareil.

*Maturity when described*.—Ripe for commercial harvesting; processing; and shipment.

*Date of first harvest*.—Approximately Jul. 27, 2015. The date of first harvest can vary between seasons based upon the current crop load, the prevailing climatic conditions, and the current cultural practices including the type and amount of irrigation being employed, and the surrounding soil conditions. Generally speaking, the nuts of the new variety typically mature with, but generally before, the crop of the 'Nonpareil' Almond tree, (unpatented) at the same geographical location.

*Date of last harvest*.—About Aug. 8, 2015.

*Nut distribution*.—The almonds are generally spread-out evenly throughout the bearing tree canopy.

*Tenacity*.—Shell adhesion is firm until harvest. Nut removal is considered thorough at harvest.

Hull:

*Surface texture*.—Relatively smooth prior to harvest but it becomes increasingly wrinkled, and withered following hull split, and nearer to the time of harvest. The hull is covered with a short fine pubescence.

*Form*.—Elliptical.

*Thickness*.—Considered very thin at the time of kernel maturity. Very little mesocarp pulp or fibers adhere to the shell.

*Flesh*.—Leathery, and becoming brittle when dry.

*Suture texture*.—Considered smooth.

*Exterior hull color*.—A dull tan color, (Approximately RHS Greyed-Orange Group 165 D).

*Internal hull color*.—A greyish orange (Approximately RHS Greyed-Orange Group 165 B).

*Typical weight*.—Approximately 5.0 grams. This characteristic is dependent upon the prevailing cultural practices, and therefore is not particularly distinctive of the new variety.

*Dehiscence*.—Very open, and widely flaring, and further having a clean separation at the suture, and throughout the mesocarp.

*Adherence*.—Very weak and easily removed in the hulling process.

Shell:

*Size*.—Large, approximately 33.0-36.0 millimeters in length; approximately 20.0-23.0 millimeters in width; and approximately 12.5-14.5 millimeters in thickness.

*Exterior shell color*.—The exterior shell color is a brownish-white (RHS Orange-White Group159 A).

*Inner shell color*.—A pale orange color (RHS Greyed-Orange 165 C).

*Surface texture*.—The surface of the shell nearer the suture exhibits shallow angled furrows ending at the suture. The remaining shell surface is covered with pitting. The inner seal of the shell is quite smooth. A sufficient space exists between the exterior of the kernel, and the shell inner seal to allow removal of the nut from the endocarp during the shelling process. The shell is sound, and durable, but can be opened by hand.

*Apex*.—Shape — Acuminate. Apex Length — approximately 2.0-3.0 millimeters.

*Apex base orientation*.—Slightly oblique toward the ventral side.

*Suture*.—Generally — A wing/fin extends away from the shell at the suture, and is present from the base to apex.

*Suture width*.—Approximately 4.0-6.0 millimeters in width. Suture Thickness — Approximately 0.05-1.0 millimeters. The Suture is totally sealed, and is resistant to ant damage.

*Stem scar/hilum*.—Relatively wide, and approximately 5.0-6.5 millimeters in width; and about 3.0-4.5 millimeters in height.

Kernel:

*Size*.—Large, approximately 24.0-30.0 millimeters in length; about 13.0-15.5 millimeters in width; and approximately 8.0-10.0 millimeters in thickness.

*Weight*.—Approximately 1.5 grams. The conditions under which the almond trees are cultured can influence individual kernel size both positively and negatively.

*Form*.—Ovate to slightly elliptical.

*Shape*.—Relatively flat in the thickness dimension. This is similar to the nut produced by the 'Nonpareil' Almond tree (unpatented). The Base is generally rounded to slightly oblique relative to the dorsal side. Still further the Apex concludes in a short fine point which is approximately 1.0 millimeter in length.

*Surface texture*.—Relatively smooth and having a slight and gentle ribbing noted between the kernel veining. This is quite similar to the nuts as produced by the 'Nonpareil' Almond tree (unpatented).

*Pellicle*.—Tenacious to the kernel meat. Medium to thin relative to the current commercially available almond varieties which are being grown. A slight pubescence is present.

*Color*.—Considered a light golden-brown, approximately (RHS Greyed-Orange Group N163 B), to a slightly darker orange color, (RHS Greyed-Orange Group 164 A). The Kernel color can vary with the prevailing growing conditions, the tree age, and the current irrigation applications which are being employed.

*Generation of double kernels*.—The variety exhibits an extremely low percentage of double (or twin) kernels. The percentage of double kernels is typically less than about 1%.

*Flavor*.—Mild, sweet and slightly fruity.

*Quality*.—The Kernel has a very high quality with a low percentage of kernel defects or ant damage.

*Use*.—The variety is useful in producing both shelled and in-shell almonds for both local and long distance markets.

*Keeping quality*.—Kernels have been stored for up to two years and have continued to have good flavor, low defects, little or no rancidification, or kernel discoloration.

*Shipping quality*.—Very good. Similar to other commercial almond varieties.

*Resistance to insects and disease*.—The present variety has exhibited a firm, durable and well-sealed suture that has resulted in virtually no damage from ants and Navel Orange Worm (*Amylose transitella*). This is quite unlike the nuts produced by the 'Nonpareil' Almond tree, (unpatented), and other existing, open-sutured varieties. The current variety has also exhibited a lower susceptibility to the fungus pathogen *Rhizopus stolonifer* (commonly known as 'hull rot', 'black mold' or 'bread mold'). It should be noted that the current variety has a degree of sensitivity to almond rust (*Tranzchelia discolor*) if normal fungus control is not practiced. Although the new variety of almond tree possesses the described characteristics when grown under the ecological conditions prevailing near Fowler, Calif., in the Central part of the San Joaquin Valley of Calif., it should be understood that variations of the usual magnitude, and characteristics incident to changes in growing conditions, fertilization, nutrition, pruning, pest control, frost, climatic variables and changes in horticultural management are to be expected.

Having thus described and illustrated our new variety of almond tree, what we claim is new, and desire to secure by Plant Letters Patent is:

1. A new and distinct variety of almond tree, substantially as illustrated and described, and which is characterized principally as to novelty by expressing self-fertility, and further producing a well-sealed nut which is ripe for harvesting and shipment on approximately July 27th to August 8th under the ecological conditions prevailing in the San Joaquin Valley of Central California.

* * * * *